United States Patent [19]
Kohno

[11] Patent Number: 5,399,867
[45] Date of Patent: Mar. 21, 1995

[54] FOREIGN PARTICLE INSPECTION APPARATUS
[75] Inventor: Michio Kohno, Tokyo, Japan
[73] Assignee: Canon Kabushiki Kaisha, Tokyo, Japan
[21] Appl. No.: 232,462
[22] Filed: Apr. 22, 1994

Related U.S. Application Data

[63] Continuation of Ser. No. 943,156, Sep. 10, 1992, abandoned, which is a continuation of Ser. No. 644,568, Jan. 23, 1991, abandoned.

[30] Foreign Application Priority Data

Jan. 26, 1990 [JP] Japan ................................. 2-15108

[51] Int. Cl.$^6$ ........................................... G01N 21/64
[52] U.S. Cl. ................................ 250/461.1; 250/459.1
[58] Field of Search ................ 250/461.1, 458.1, 459.1

[56] References Cited

U.S. PATENT DOCUMENTS

| | | | |
|---|---|---|---|
| 4,087,685 | 1/1978 | Froot | 250/461.1 |
| 4,200,801 | 4/1980 | Schuresko | 250/458.1 |
| 4,236,082 | 11/1980 | Butler | 250/461.1 |
| 4,336,459 | 6/1982 | Fay | 250/461.1 |
| 4,744,663 | 5/1988 | Hamashima et al. | 250/461.1 |
| 4,800,282 | 1/1989 | Nishimura | 250/461.1 |
| 4,816,686 | 3/1989 | Hara et al. | 250/459.1 |
| 4,877,965 | 10/1989 | Dandliker et al. | 250/458.1 |
| 5,067,811 | 11/1991 | Ouchi | 356/121 |

FOREIGN PATENT DOCUMENTS 61-182238 8/1986 Japan .
61-222145 10/1986 Japan .
64031417 2/1989 Japan .

Primary Examiner—Carolyn E. Fields
Attorney, Agent, or Firm—Fitzpatrick, Cella, Harper & Scinto

[57] ABSTRACT

A foreign particle inspection arrangement includes an optical illumination system that irradiates a predetermined area of a substrate surface with fluorescence exciting ultraviolet light pulses. Fluorescence from a foreign particle on the substrate is directed by an optical detection system to a photoelectric transducer which detects accumulation of fluorescence in response to plural ultraviolet light pulses. An electrical processing system inspects the adherence of the foreign particle to the substrate on the basis of the photoelectric transducer output. A position determining type of photoelectric transducer such as a charge coupled array or pickup tube may be used to determine the position of the foreign particle to avoid misdetection due to readherence. The illumination of a large area keeps the radiation density low to prevent damage to a reticle pattern on the substrate.

16 Claims, 5 Drawing Sheets

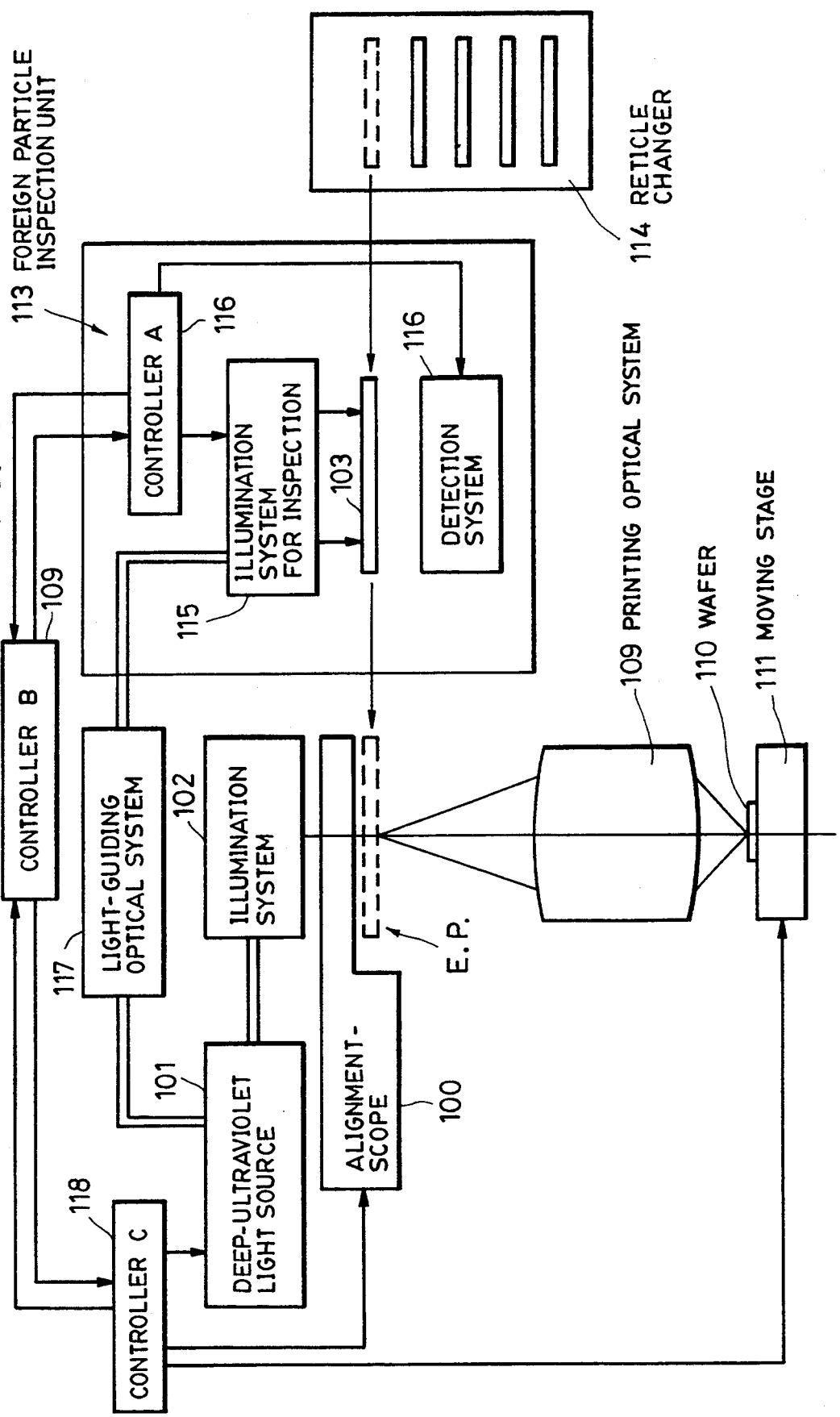

FOREIGN PARTICLE INSPECTION APPARATUS

This application is a continuation of application Ser. No. 07/943,156, filed Sep. 10, 1992, now abandoned, which is a continuation of application Ser. No. 07/644,568, filed Jan. 23, 1991, abandoned.

BACKGROUND OF THE INVENTION

1. Field of the Invention

This invention relates to surface state inspection apparatus, and more particularly, to surface state inspection apparatus which is suitable for detecting foreign particles, such as opaque dust or the like, other than a circuit pattern, adhered to a substrate, such as a reticle, a photomask or the like, in the semiconductor production process using a deep-ultraviolet-light exposure method.

2. Description of the Prior Art

In the IC (integrated circuit) production process, in general, an IC is produced by transferring a circuit pattern for exposure formed on a substrate, such as a reticle, a photomask or the like, to the surface of a wafer coated with or a resist using a semiconductor printing apparatus (a stepper or a mask aligner).

At this time, if a foreign particle, such as dust or the like, is present on the surface of the substrate, the foreign particle is also transferred in the transfer operation, causing a decrease in the yield of the IC production.

Particularly when a circuit pattern is repeatedly printed on the surface of a wafer by a step-and-repeat method using a reticle, one foreign particle on the surface of the reticle is printed on the entire surface of the wafer, causing a large-decrease in the yield of the IC production.

Accordingly, it is indispensable to inspect the presence of foreign particles on a substrate in the IC production process, and various kinds of inspection methods have been proposed. Particularly, inventions have been disclosed in U.S. Pat. No. 4,800,282 (which corresponds to Japanese Patent Application Public Disclosure (Kokai) No. 61-182238 (1986)) and Japanese Patent Application Public Disclosure (Kokai) No. 61-222145 (1986)). According to these inventions, an ultraviolet beam is merely projected or projected while being scanned onto the surface of a wafer or a semiconductor substrate to detect fluorescence issued from a foreign particle remaining on the surface of the wafer or substrate.

However, two kinds of apparatus described in the above-described publications have the following disadvantages: a first apparatus for detecting the presence of a remaining photoresist, serving as foreign particles, on a wafer only detects fluorescence generated when the wafer is merely irradiated by light only with a single detector, the position of the remaining photoresist cannot not identified. If a foreign particle is detected by a spot scanning method, that is, by scanning the wafer with a beam, as in a second apparatus, the position of the foreign particle can be identified in principle. However, the position of the foreign particle moves in some cases on a reticle in the course of inspection. Accordingly, even if, for example, only one foreign matter is present on the reticle, the apparatus misdetects as if a plurality of foreign particles were present on the reticle if the movement of the foreign particle occurs several times in the course of inspection.

SUMMARY OF THE INVENTION

The present invention has been made in consideration of the above-described disadvantages of the prior art.

It is an object of the present invention to provide a foreign particle inspection apparatus which can securely detect the presence and position of a foreign particle without misdetection due to readherence of dust, or the like.

The invention is directed to apparatus for inspecting foreign particles on a surface in which a predetermined region of the surface is illuminated by irradiating the region with a fluorescence exciting light.

An optical detection system images the illuminated predetermined region. Detection means provided on an imaging surface has a light position determining function.

The fluorescence issued from a foreign particle on the surface is detected and its state is inspected.

The foregoing and other objects and features of the present invention will become more apparent from the following detailed description of the preferred embodiments.

BRIEF DESCRIPTION OF THE DRAWINGS

FIG. 5 is a diagram showing the configuration of a fourth embodiment of the present invention.

DESCRIPTION OF THE PREFERRED EMBODIMENTS

Figure 1:
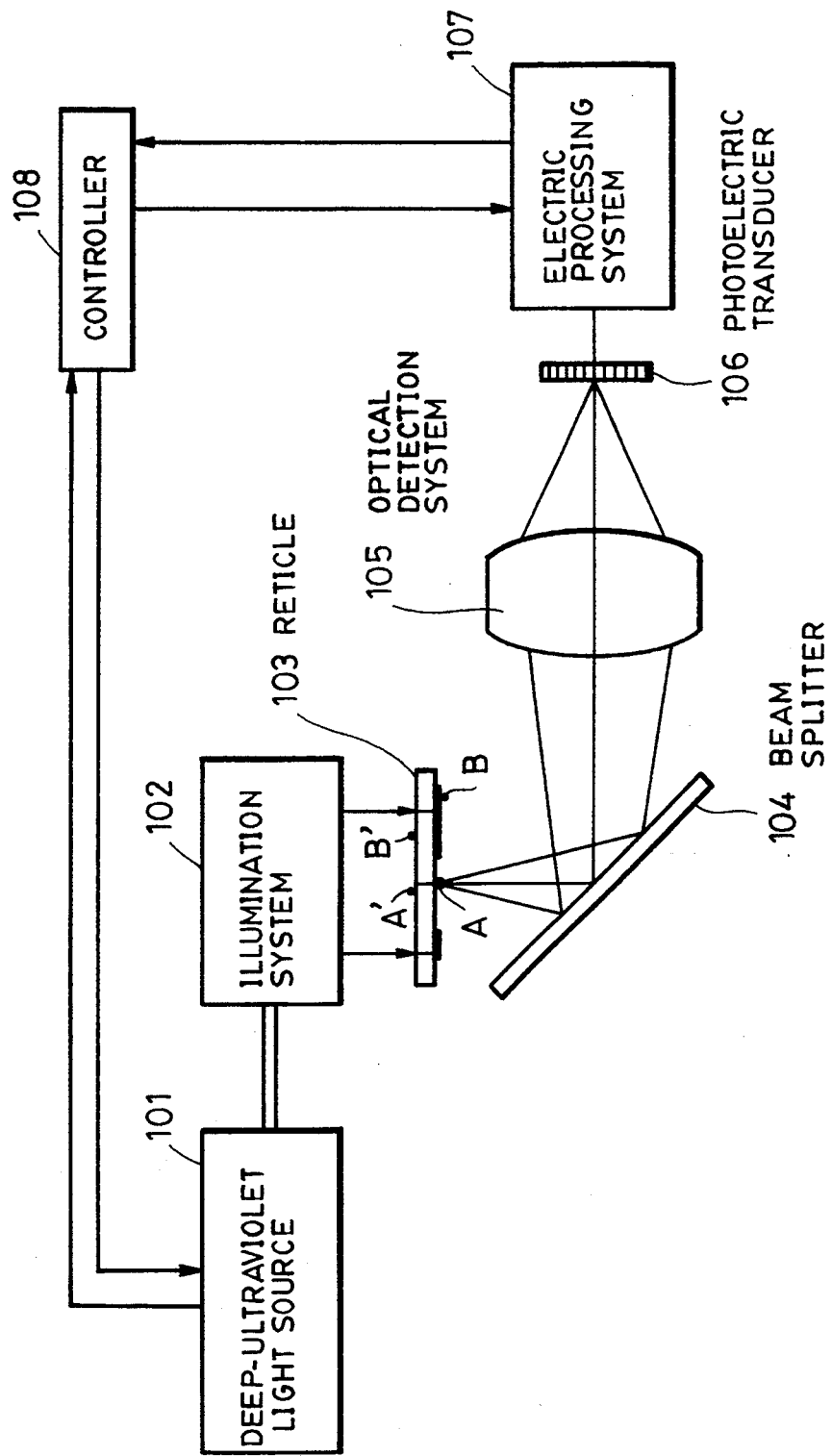
FIG. 1 is a diagram showing the configuration of a first embodiment of the present invention.

FIG. 1 is a diagram showing the configuration of a foreign particle inspection apparatus according to a first embodiment of the present invention.

In FIG. 1, there is shown a deep-ultraviolet light source 101, such as an excimer laser. An illumination system unit 102 uniformly and simultaneously (all at once; not sequence like scanning) illuminates the entire region of the surface of a reticle 103 to be inspected from above in the direction vertical to the surface of the reticle 103 with a predetermined NA (numerical aperture). A beam splitter 104 is provided under the reticle 103. The beam splitter 104 functions as follows: That is, a deep-ultraviolet light beam passing through the reticle 103 passes through the beam splitter 104 as it is. When irradiated by deep-ultraviolet light, a foreign particle, such as dust or the like, adhered to the substrate of the reticle generally emits fluorescence having specific wavelengths in the visible region in accordance with its constituent atoms. The beam splitter 104 designed to reflect the wavelength region of the fluorescence, and to transmit the wavelength of the irradiating light. Hence, only the fluorescence from the foreign particle is guided to an optical detection system after the beam splitter 104. It is thereby possible to increase the detection probability of foreign particles. A detection optical system 105 produces a reduced image of a surface of the reticle 103, particularly, the surface having a circuit pattern (the lower surface in FIG. 1) onto the surface of a photoelectric transducer 106.

It is desired to use a device capable of determining the position of light as the photoelectric transducer 106, such as a two-dimensional CCD (charge-coupled device) array or a pickup tube, because such a device can determine to which position on the reticle a foreign particle adheres. A time needed to detect the image is sufficiently smaller than a time needed when the above-described scanning is performed.

The output from the photoelectric transducer 106 is processed by an electric processing system 107, whose timing is controlled by a host controller 108 in synchronization with an emission state of the deep-ultraviolet light source 101. When, for example, an excimer laser is used as the deep-ultraviolet light source 101, and a two-dimensional CCD array is used as the photoelectric transducer 106, the control is performed as follows:

An excimer laser oscillates only in pulsed manner according to its operating principle, and its oscillation frequency may, for example, be about 200 Hz (hertz). A CCD array can change a time for receiving the amount of light near 20 msec (milliseconds) freely to some extent. Accordingly, if the amount of light of fluorescence is small, or it is intended to increase the resolution of a foreign particle, emission pulses of the excimer laser may be stored a plurality of times by sufficiently increasing the light receiving time of the CCD array to the extent that the above-described problem caused by readherence of dust does not occur, and signal processing, such as digitizing the output of the CCD array with a predetermined slicing operation, may be performed.

Figure 2:
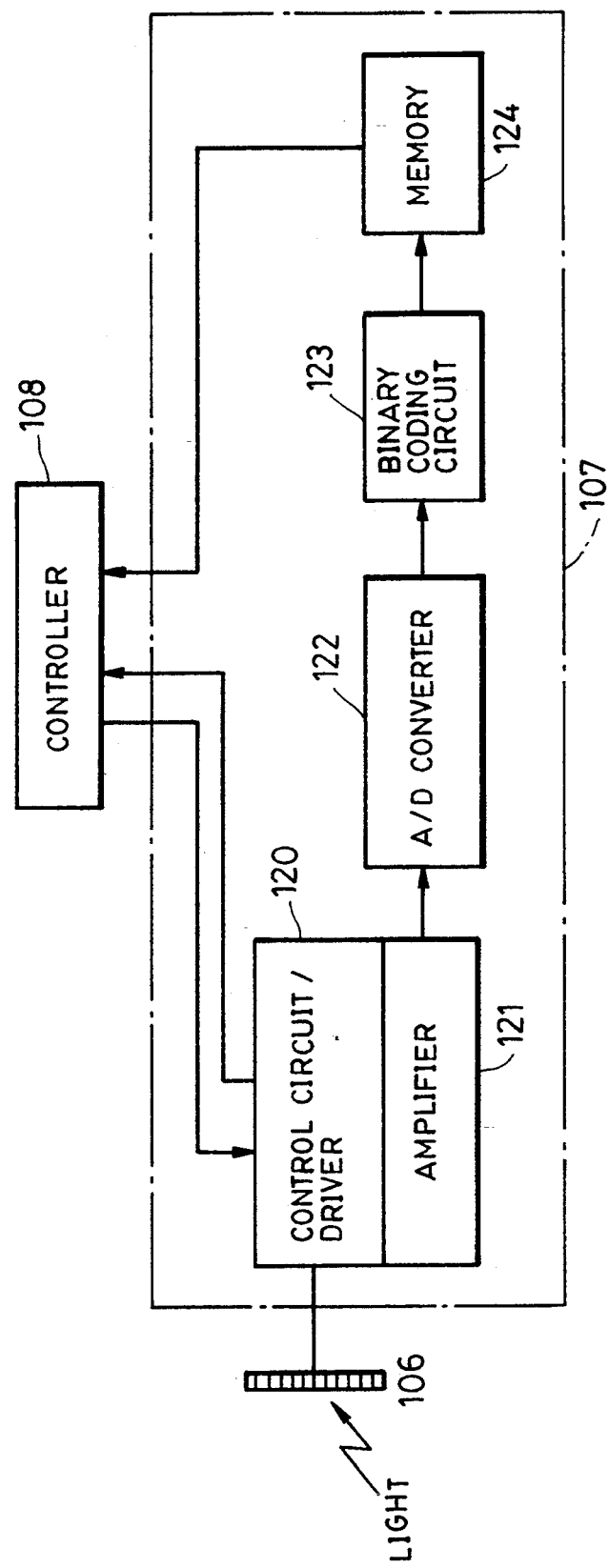
FIG. 2 is a diagram showing the configuration of an electric processing circuit used in the FIG. 1 embodiment.

FIG. 2 shows the electric processing system 107 in greater detail.

In FIG. 2, an output from the photoelectric transducer 106 is first stored in a gate of a control circuit/driver 120 in accordance with a timing command from the controller 108, and is then output. The output from the control circuit/driver 120 is first amplified by an amplifier 121, and is then subjected to analog-to-digital conversion by an A/D converter 122. The converted digital signal is ranked by a binary coding circuit 123 according to the presence/nonpresence of dust or the magnitude of the signal with a preset sensitivity, and is stored in a memory 124 together with the position data of the dust.

Once the output of the photoelectric transducer 106 has been issued, a signal is sent to the controller 108, which sends a command to the light source 101 to demand the next emission. This operation is repeatedly performed.

in FIG. 1, the illuminating light is irradiated from above the reticle 103, and the fluorescence detection system is provided at the lower side (transmission side) the reticle 103. In this arrangement, only dust particles (particles A and A' in FIG. 1) adhered to transparent portions on the substrate are detected, and dust (particle B in FIG. 1) adhered to the pattern is not illuminated. Although dust (particle B' in FIG. 1) adhered to portions corresponding to pattern portions on the surface opposite to the pattern is illuminated, the dust is not detected because fluorescence from it is shielded by the pattern. As shown in a third embodiment (FIG. 4) which will be described later, also when a reticle pattern is actually transferred to a wafer using a printing apparatus, a reticle is set in the above-described arrangement. Hence, dust particles which are transferred to a wafer to become common defects are only particles A and A'. The image of the particle A is transferred to the wafer. The image of the particle A' is defocused, causing unevenness in illuminance. Particles B and B' do not influence printing at all, because they are hidden by the pattern. That is, by adopting the above-described arrangement, only minimum necessary dust particles are detected. Since a reticle cannot be washed more often than necessary, the present apparatus increases efficiency in the entire production process.

Although, in FIG. 1, the wavelengths of the deep-ultraviolet illuminating light and the fluorescence of the foreign particle are separated by the beam splitter 104, the separation method is not limited to this method. For example, the beam splitter 104 may be replaced by a mere reflection mirror, and, instead, an optical filter having a characteristic that cuts off the deep-ultraviolet light and transmits the visible light (for example, transmit wavelengths greater than or equal to 400 nm) may be provided within the detection optical system 105.

In some cases, known impurity substances are contained within the glass substrate of a reticle or within chromium used for a pattern. Fluorescence spectra of such impurities are also known. For example, impurities within the glass emit red fluorescence.

In order to cut such noise, an optical filter to cut the wavelength region of the fluorescence may be added within the beam splitter 104 or the detection optical system 105.

As described above, the present apparatus simultaneously irradiates a fluorescence generating exciting light onto a predetermined area on a mask or a reticle. The fluorescence emitted from a foreign particle, such as dust or the like, adhered to the substrate is received and stored in a photoelectric conversion device that determines the position of light to detect the presence of the foreign particle. Since information can be obtained instantaneously or in a short time, misdetection due to readherence of dust, or the like can be substantially avoided. Chromium or chromium oxide which is usually used as a material for a circuit pattern on a substrate, and quartz which is used as a material for a glass substrate do not generate fluorescence when irradiated by exciting light. Hence, according to the present method, it is possible to detect a foreign particle on a substrate having a pattern while automatically discriminating the foreign particle from the pattern.

Figure 3:
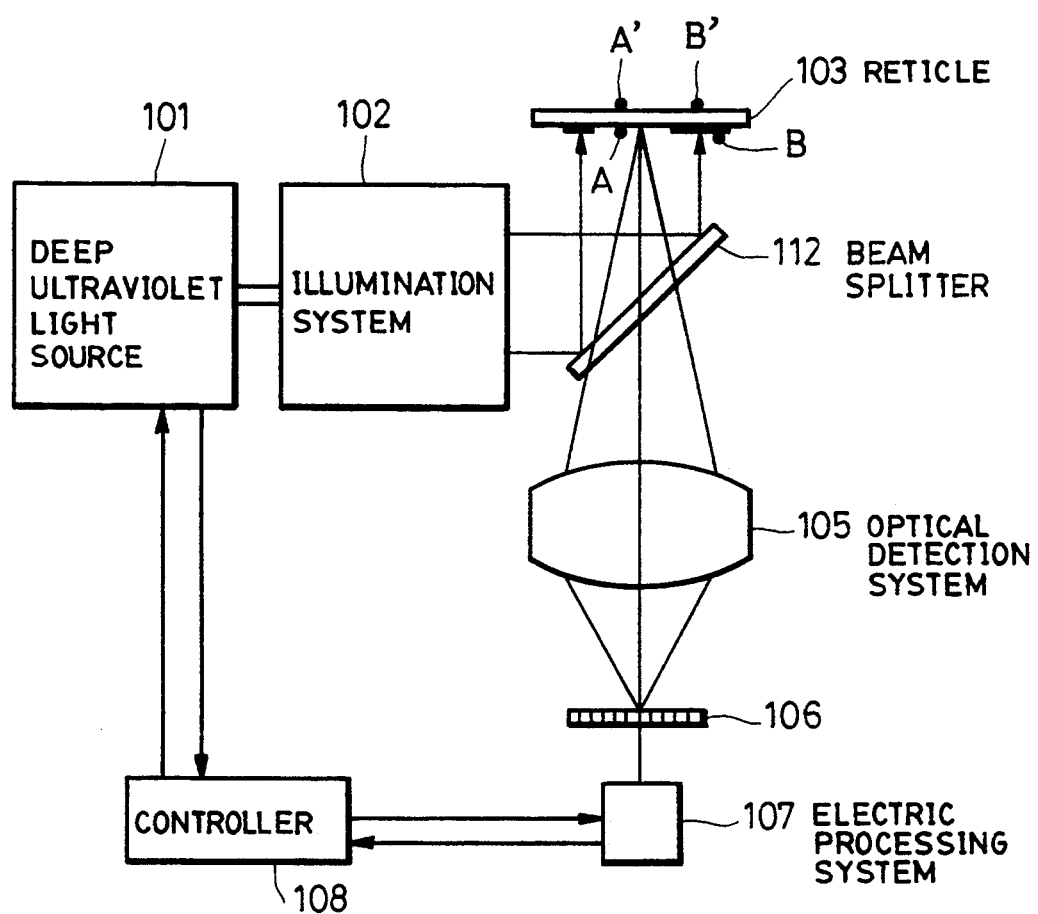
FIG. 3 is a diagram showing the configuration of a second embodiment of the present invention.

FIG. 3 shows a second embodiment of the present invention.

While the illuminating light beam is projected from above the reticle in the FIG. 1 embodiment, in the present embodiment, the light is projected from below the reticle (from the side of the pattern). In this arrangement, any foreign particle on the surface of the pattern can be detected no matter whether it adheres to a transparent portion (particle A in FIG. 3) or to the pattern (particle B in FIG. 3).

When dust adheres by static electricity, even if a dust particle has adhered to the pattern during inspection (particle B in FIG. 3), it may move and adhere to the transparent portion (particle A in FIG. 3) while the reticle is set to the exposing position. Accordingly, when it is considered necessary to inspect all the dust particles on the pattern surface, the present method in which the illuminating light is irradiated from the side of the surface to be inspected (the pattern surface in the case of FIG. 3) is suitable, and dust particles are detected on the same side. A beam splitter 112 used in the present embodiment has a characteristic reverse to that of the beam splitter 104 shown in FIG. 1. That is, the beam splitter 112 reflects the deep-ultraviolet light, and transmits the visible light.

Also in FIG. 3, a foreign particle (particle B' in FIG. 3) adhered to portions corresponding to pattern portions on the surface opposite to tile pattern is not detected. In order to securely detect even such a foreign particle, after first inspecting the pattern surface in the state shown in FIG. 3, the reticle may be turned upside down, and the surface opposite to the pattern may be inspected again. Alternatively, another illumination and detection system pair such as shown in FIG. 3 may be provided at the back side (upper side) of the reticle, or a system for detecting the surface of the reticle opposite to the pattern may be separately provided while the surface of the reticle opposite to the pattern is irradiated with an illuminating light beam guided from the same light source.

Figure 4:
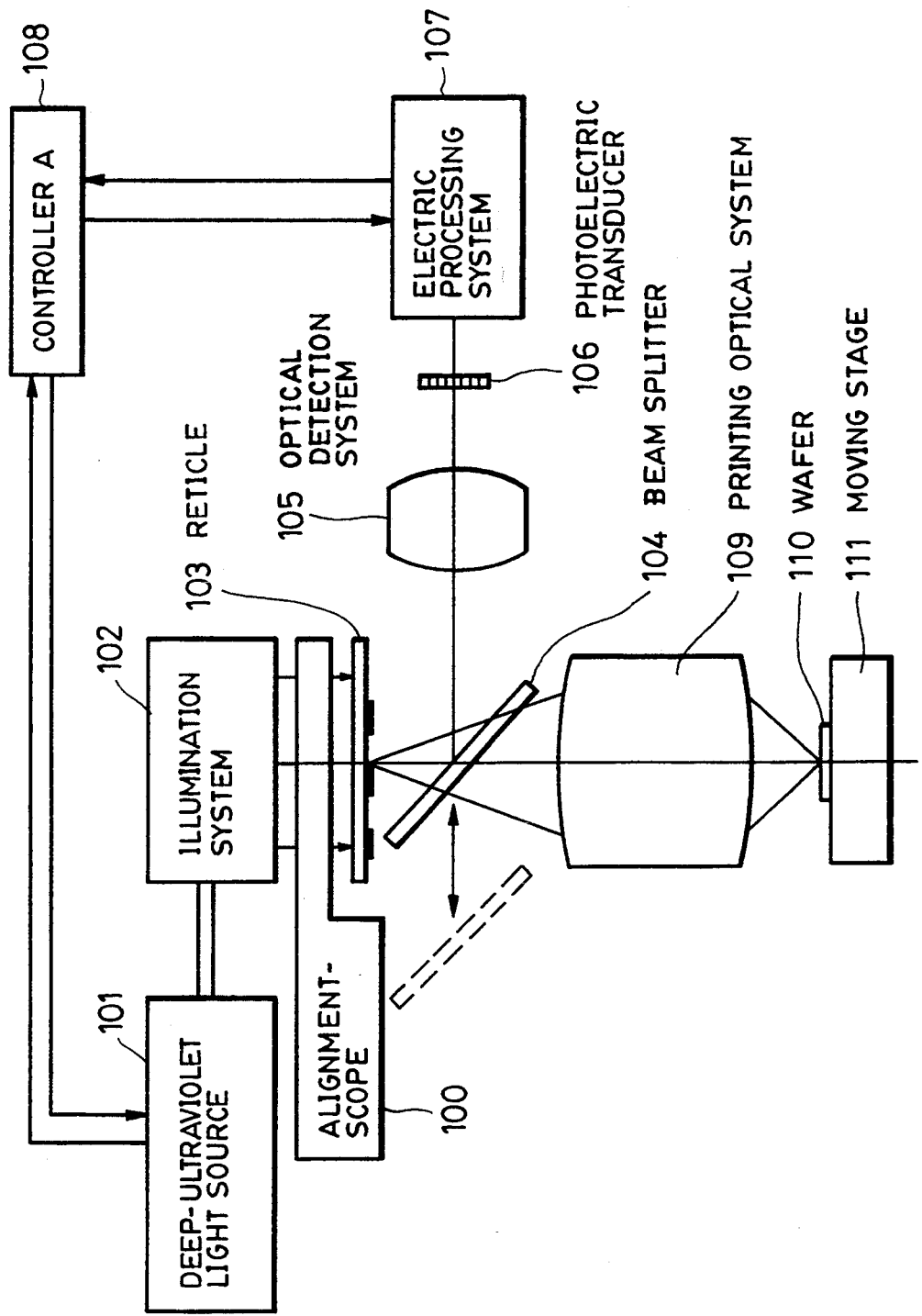
FIG. 4 is a diagram showing the configuration of a third embodiment of the present invention.

FIG. 4 shows a third embodiment of the present invention.

In this embodiment, a reticle is set to the exposing position of a semiconductor printing apparatus, and the method of the first embodiment is applied without modification.

That is, in the present embodiment, a foreign particle is inspected using a deep-ultraviolet exposure and illumination system 102 of the printing apparatus. The detection system is the same as in FIG. 1.

An ultrahigh-resolution lens system (or a mirror system) 109 is used to transfer a reticle pattern onto a wafer 110. During a printing operation, the wafer 110 is exposed while being successively shifted by one step in accordance with a stepwise movement of a moving stage 111. An alignment-scope optical system 100 for aligning a reticle with the wafer includes at least one microscope system for observing the reticle.

A beam splitter 104 is inserted within the printing optical path when inspecting foreign particles on the reticle, and is moved to the outside of the optical path (a position indicated by broken lines in FIG. 4) during a printing operation. If the resolution performance of the printing optical system 109 is corrected to include the beam splitter 104, the beam splitter 104 may be fixed within the optical path.

By inspecting the reticle immediately before an exposing operation in a state wherein the setting of the reticle to its exposing position has been completed, as in the present embodiment, reliability in inspection is greatly increased.

To the contrary, if the reticle is inspected by an independent inspection system outside the printing apparatus, a problem may arise in that new dust may adhere until the reticle is conveyed to the printing apparatus and is set to the exposing position.

Although, in the present embodiment, the foreign particle inspection system (104, 105, 106 and 107) is provided separately from the alignment-scope 100, the inspection system may be provided within the optical system of the alignment scope. The entire apparatus can thereby be simplified.

In the embodiments shown in FIGS. 1 through 4, the entire region to be inspected of the reticle may be simultaneously illuminated, and may be imaged onto the surface of the photoelectric transducer all at once. The energy density of the illuminating light beam, however, decreases in that case. As a result, the necessary detection sensitivity may not be obtained even if the storage time of the fluorescence in the photoelectric transducer is increased as much as possible.

In such a case, the region to be inspected of the reticle may be divided. One divided region may be simultaneously (all at once) irradiated, and the irradiated region may be imaged onto the surface of the device to perform inspection. In order to inspect the entire region to be inspected, a mechanism may be provided wherein a mechanical means performs a stepwise feed operation of the reticle.

FIG. 5 shows a fourth embodiment of the present invention.

In this embodiment, a foreign particle inspection system according to the present invention is incorporated in a semiconductor printing apparatus as one unit. A reticle changer 114 is a unit which contains a plurality of reticles waiting for the use. A foreign particle inspection unit 113 includes all the necessary components shown in FIG. 1. The until 113 inspects foreign particles on a reticle drawn from the changer 114 before the reticle is set to an exposing position (position E.P. in FIG. 5). It is necessary to provide a system, which guides a light beam from a deep-ultraviolet light source 101 to an illumination system for inspection, and changes between the light source 101 and a printing illumination system 102. An optical system 117 guides the light beam for that purpose.

An excimer laser is expensive, large in size, and hence occupies a large floor area. Accordingly, it is difficult to use two excimer lasers in one printing apparatus except particular cases, and therefore many disadvantages exist in using them. Accordingly, it is necessary to provide controllers in order to properly use one excimer laser both for inspection and printing purposes with a certain timing.

The entire sequence of a stepper itself is controlled by a command system comprising several hierarchical steps. A controller C 118 shown in FIG. 5 is provided for that purpose, and controls the sequence of alignment, exposure, and stepwise feed of a wafer, which are basic operations of a stepper. A controller A 116 incorporated within the foreign particle inspection unit 113 controls illuminating light for inspecting a reticle, an electric processing system for detection, and the feed state of a reticle during inspection, as explained in FIG. 1. The controllers A and C are controlled by host controller B 109. That is, the controller B 109 outputs control signals so as to properly use the same excimer-laser light source 101 both for exposing a wafer and for inspecting a reticle, and to reduce the loss time of the entire system as much as possible. In order to provide such efficiency, the controller B 109 guides the light beam from the light source 101 to an illumination system 115 for inspecting a reticle, for example, during sequence operations (alignment, a feeding and drawing operation of a wafer, and the like) other than exposure on a wafer. Alternatively, the light beam may be guided to the system 115 between exposing operations of respective chips (during stepwise feed). If ultraviolet light so strong as to produce fluorescence is concentrated on one point on a reticle pattern even within a short time, an etched pattern (chromium or chromium oxide in the case of a reticle) on the substrate can be severely damaged.

In the foregoing embodiments, since a light beam irradiates a large area, the irradiation density on the reticle is relatively small. Hence, the reticle pattern is not damaged, and a foreign particle is not blown away. Another disadvantage in the prior art is partial omission of inspection on a reticle. This happens when an excimer laser is used as the deep-ultraviolet light source. An excimer laser (having a wavelength of 248 nm, 198 nm or the like) currently being studied as a light source for photolithography emits pulsed light. The duration of a pulse may be as short as 10–20 nsec (nanoseconds) at most, and its repetition frequency is about 200 Hz. When using the beam scanning method as described in the above-described publications, one line of a beam must be scanned within 10–20 nsec. If the scanning time is longer, the laser pulse is turned off halfway. While the laser pulse is turned off, foreign particles that may be on the substrate cannot be detected.

However, since the size of the substrate is about 100 mm square, it is impossible to uniformly scan this distance with the beam within 10–20 nsec by the current technique.

In the foregoing embodiments, since the entire region to be inspected or the entire divided region is simultaneously (all at once) irradiated, partial omission of inspection as in spot scanning never occurs. An inherent problem of an excimer laser is wavelength peculiarity. That is, it is known that, even if an optical component, such as reticle, is transparent for wavelengths of continuously oscillating laser light used for scanning in conventional known examples, it is in some cases opaque for short wavelengths of, for example, excimer laser light. For example, it is well known that, if excimer laser light having a high illuminance is projected on quartz, serving as the substrate for a reticle, for a long time, defects, such as color centers, are produced. The presence of the color centers can be clearly observed when excimer laser light is irradiated thereupon because the defect portions emit light. However, it is difficult to detect the defect portions by observing them only using the visible light without irradiating them by excimer laser light. The shortest wavelength of a laser which can be used with a continuous oscillation mode is 325 nm of a HeCd laser. Actually, laser wavelengths which are most widely used for inspection are 442 nm (HeCd), 488 nm (Ar$^{30}$), 515 nm (Ar+), 633 nm (HeNe) and the like. These wavelengths cannot replace 248 nm (KrF) and 198 nm (ArF) of excimer laser light. The use of an excimer laser as in the foregoing embodiments has the advantage of being capable of performing inspection with the same light as used for exposure, as well as the physical advantage peculiar to excimer laser light that defects opaque to the wavelengths of excimer laser light can be detected in the form of fluorescence.

The present invention has the effects that it is possible to simply discriminate between a pattern and dust, and to exactly inspect for adherence of dust.

As a result, it is possible to increase reliability in reticle inspection in the semiconductor printing process using a deep-ultraviolet light source represented by an excimer laser, and to greatly increase the yield in the semiconductor production.

An object to be inspected is not limited to a reticle, but, for example, a wafer may also be inspected. When inspecting a wafer, by irradiating deep-ultraviolet light for inspection vertical to a surface to be inspected, for example, by arranging the optical axis of an illumination system for inspection vertical to the surface, the present invention makes it possible to reduce the number of foreign particles which are overlooked in the shadow of large projections and recesses, such as those of a pattern.

What is claimed is:

1. An apparatus for inspecting a surface of an object, comprising:
    illumination means for irradiating ultraviolet light pulses for generating fluorescence onto a predetermined region of the object;
    detection means including an accumulation type photoelectric transducer for detecting accumulation of the fluorescence from said predetermined region in response to a plurality of the irradiating ultraviolet light pulses; and
    inspecting means for inspecting a surface condition of the object on the basis of a result of detection by said detection means.

2. An apparatus to claim 1, wherein said detection means further comprises an optical system for imaging the predetermined region onto the photoelectric transducer.

3. An apparatus according to claim 1, wherein said detection means further comprises an optical element for separating said fluorescence from the ultraviolet light pulses.

4. An apparatus according to claim 1, wherein said photoelectric transducer comprises a CCD array.

5. An apparatus according to claim 1, wherein said illumination means comprises an excimer laser source.

6. An apparatus according to claim 1, wherein said inspecting means inspects a foreign particle on the object.

7. A method for inspecting a surface of an object, comprising:
    irradiating ultraviolet light pulses for generating fluorescence onto a predetermined region of the object;
    detecting integration of the fluorescence from said predetermined region irradiated by said irradiating ultraviolet light pulses; and
    inspecting a surface condition of the object on the basis of a result of said detecting.

8. An exposure apparatus, comprising:
    an inspection system for inspecting a surface of a substrate having a pattern; and
    an exposure system for performing pattern transfer, said exposure system including an optical system for irradiating exposure light onto the substrate;
    said inspection system comprising:
        illumination means for irradiating ultraviolet light pulses for generating fluorescence onto a predetermined region of the substrate;
        detection means, including an accumulating type photoelectric transducer, for detecting accumulation of the fluorescence from said predetermined region in response to a plurality of the irradiating ultraviolet light pulses; and
        inspecting means for inspecting a surface condition of the substrate on the basis of a result of detection by said detection means.

9. An apparatus according to claim 8, wherein said exposure system comprises a light source for said ultraviolet light pulses, and the light source generates both the exposure light and the ultraviolet light pulses.

10. An apparatus according to claim 8, wherein said illumination means comprises an excimer laser source.

11. An apparatus according to claim 8, further comprising an alignment system for aligning the substrate with a material to be exposed.

12. A semiconductor device manufacturing method, comprising:
    preparing a reticle having a circuit pattern and a wafer;

inspecting a surface of the reticle; and printing the circuit pattern onto the wafer by irradiating exposure light onto the reticle;

wherein said inspecting step comprises the steps of:

irradiating ultraviolet light pulses for generating fluorescence onto a predetermined region of the reticle;

detecting accumulation of the fluorescence from said predetermined region by an accumulating type photoelectric transducer in response to a plurality of said irradiating ultraviolet light pulses; and inspecting a surface condition of the reticle on the basis of a result of said detecting.

13. A method according to claim 12, further comprising aligning the reticle with the wafer.

14. A method according to claim 12, said printing step comprises a step-and-repeat sequence.

15. A method according to claim 12, wherein said exposure light comprises an excimer laser light.

16. A semiconductor device manufactured by a method comprising the steps of:

preparing a reticle having a circuit pattern and a wafer;

inspecting a surface of the reticle; and printing the circuit pattern on the wafer by irradiating exposure light onto the reticle;

wherein said inspecting step comprises the steps of:

irradiating ultraviolet light pulses for generating fluorescence onto a predetermined region of the reticle;

detecting accumulation of the fluorescence from said predetermined region by an accumulating type photoelectric transducer in response to a plurality of said irradiating ultraviolet light pulses; and inspecting a surface condition of the reticle on the basis of a result of said detecting.

* * * * *

UNITED STATES PATENT AND TRADEMARK OFFICE
CERTIFICATE OF CORRECTION

PATENT NO. : 5,399,867
DATED : March 21, 1995
INVENTOR(S) : MICHIO KOHNO

Page 1 of 2

It is certified that error appears in the above-identified patent and that said Letters Patent is hereby corrected as shown below:

ON TITLE PAGE

In [56] References Cited, under FOREIGN PATENT DOCUMENTS:
"64031417  2/1989  Japan" should read
--64-031417  2/1989  Japan--.

COLUMN 1

Line 34, "large-decrease" should read --large decrease--.
Line 58, "not" (second occurrence) should read --be--.

COLUMN 3

Line 50, "in" should read --In--.

COLUMN 7

Line 40, "($Ar^{30}$)," should read --($Ar^*$),--.

COLUMN 8

Line 14, "apparatus" should read --apparatus according--.

UNITED STATES PATENT AND TRADEMARK OFFICE
CERTIFICATE OF CORRECTION

PATENT NO. : 5,399,867
DATED : March 21, 1995
INVENTOR(S) : MICHIO KOHNO

It is certified that error appears in the above-identified patent and that said Letters Patent is hereby corrected as shown below:

<u>COLUMN 9</u>

Line 20, "said" should read --wherein said--.

Signed and Sealed this

Eighteenth Day of July, 1995

Attest:

BRUCE LEHMAN

Attesting Officer  Commissioner of Patents and Trademarks